United States Patent [19]

Agreda et al.

[11] 4,435,595

[45] Mar. 6, 1984

[54] REACTIVE DISTILLATION PROCESS FOR THE PRODUCTION OF METHYL ACETATE

[75] Inventors: Victor H. Agreda; Lee R. Partin, both of Kingsport, Tenn.

[73] Assignee: Eastman Kodak Company, Rochester, N.Y.

[21] Appl. No.: 371,626

[22] Filed: Apr. 26, 1982

[51] Int. Cl.$^3$ .............................................. B01D 3/36
[52] U.S. Cl. ..................................... 560/234; 203/35; 203/DIG. 6
[58] Field of Search .................. 560/1, 129, 231, 234, 560/235, 239, 248; 203/28, 34, 38, DIG. 6; 202/158; 422/187

[56] References Cited

U.S. PATENT DOCUMENTS 4,370,491  1/1983  Bott et al. ..................... 203/DIG. 6

FOREIGN PATENT DOCUMENTS 60717  9/1982  European Pat. Off. .
60719  9/1982  European Pat. Off. .

*Primary Examiner*—Frank Sever
*Attorney, Agent, or Firm*—David E. Cotey; Daniel B. Reece, III

[57] ABSTRACT

The present invention provides a process for the production of high purity methyl acetate from methanol and glacial acetic acid wherein the acetic acid functions both as a reactant and as an extractive agent. The process comprises countercurrently flowing approximately stoichiometric quantities of acetic acid and methanol through a single reactive distillation column in the presence of an acidic catalyst which is preferably sulfuric acid. The column provides intimate contact between the acetic acid and the methanol and between the acetic acid and the azeotropes (methyl acetate/water and methyl acetate/methanol) which are formed in the column. At preferred catalyst concentrations, the residence time in the column is at least about two hours. The process further comprises continuously removing high purity methyl acetate from the top of the column and continuously removing water from the bottom of the column. In preferred embodiments, the process further comprises removing intermediate boiling compounds, such as methyl propionate, methyl butyrate, isopropyl acetate, and mixtures thereof, from a vapor sidedraw stream. The invention further comprises in preferred embodiments the use of a temperature control scheme whereby the overhead and the bottoms compositions are controlled by using two temperature control loops.

28 Claims, 3 Drawing Figures

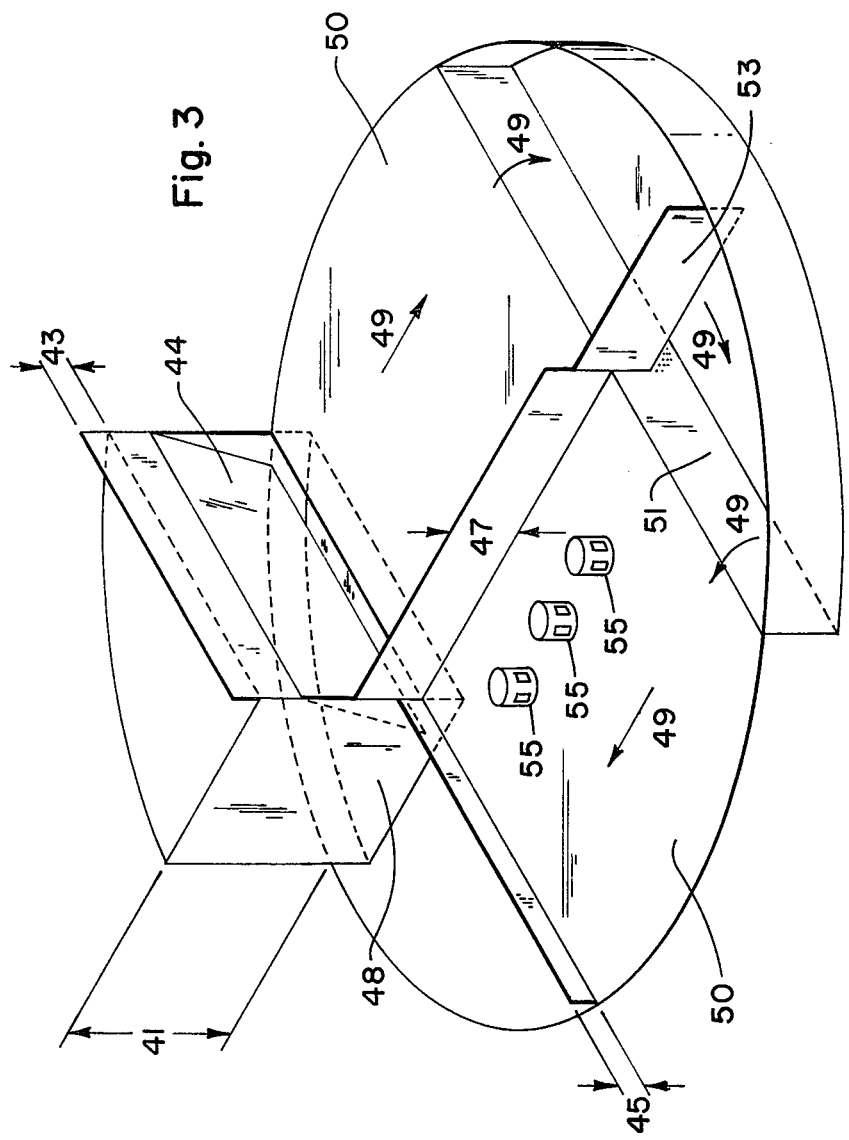

REACTIVE DISTILLATION PROCESS FOR THE PRODUCTION OF METHYL ACETATE

Description

Background of the Invention

The present invention relates to a process for the production of methyl acetate by reactive distillation. An extensive body of literature exists on the subject of reactive distillation. However, a reactive distillation process for the production of pure methyl acetate has not hitherto been disclosed.

U.S. Pat. No. 1,400,849 discloses the reaction of dilute acetic acid or vinegar with methyl alcohol in a distillation/reaction apparatus. The dilute acetic acid and methanol are fed at opposite ends of the reactor and are subjected to countercurrent flow. However, the patent does not recognize the formation of azeotropes, and there is no means, either explicit or inherent, by which the azeotropes may be broken prior to recovery of the product. Thus, the product which is recovered must be impure methyl acetate. It may be noted that the process system there disclosed includes a partial condenser (dephlegmator) in an attempt to purify the product. While the dephlegmator may be effective in the removal of a small amount of methanol from the system, it is incapable of breaking the azeotropes which are present. In another disclosed embodiment, glacial acetic acid is reacted with methanol in an apparatus which includes a single inlet pipe leading from a mixing tank to which the reactants are provided. Such a system would likewise be totally incapable of yielding a product which is free from azeotropes.

More recently, the reactive distillation of methanol and acetic acid in a packed column using sulfuric acid as the catalyst has been disclosed (Pilavakis, P. A., 1974, Ph.D. Thesis, University of London). From a practical standpoint, the process described is totally unsatisfactory. Very low conversions were achieved, the product and waste stream compositions contained large concentrations of unreacted feeds, and the product methyl acetate was of very low purity.

In contrast to the prior art described above, the present invention provides a process for the production of high purity methyl acetate from methanol and acetic acid. In the process of the present invention, acetic acid is used both as a reactant and as an extractive agent for breaking the azeotropes which are formed in the system. The process of the present invention provides a residence time which is sufficient to obtain high purity methyl acetate with high conversion of the reactants. In addition, a control scheme which enables the attainment of high distillate purity and low reactant losses is provided. Thus, the present invention allows the attainment of high reactant conversions in a single reactor/distillation column and overcomes the problem of azeotrope formation during the production of methyl acetate from methanol and acetic acid by providing a method for breaking the azeotropes in the system.

Summary of the Invention

The present invention provides a process for the production of high purity methyl acetate from methanol and glacial acetic acid wherein the acetic acid functions both as reactant and as extractive agent. The process comprises the steps of (a) counter-currently flowing approximately stoichiometric quantities of acetic acid and methanol through a single reactive distillation column in the presence of a catalytic amount of an acidic catalyst so as to provide intimate contact in the column between the acetic acid and methanol, between the acetic acid and methyl acetate/water azeotrope, and between the acetic acid and methyl acetate/methanol azeotrope, the residence time in the column being sufficient to accomplish high reactant conversion and to obtain high purity methyl acetate, and (b) continuously removing high purity methyl acetate from the top of the single column and continuously removing water from the bottom of the column.

Description of the Drawings

FIG. 3 is an illustration of a bubble cap tray design which is suitable for use in a reactive distillation column which may be used in the process of the present invention.

Detailed Description of the Invention

Figure 1:
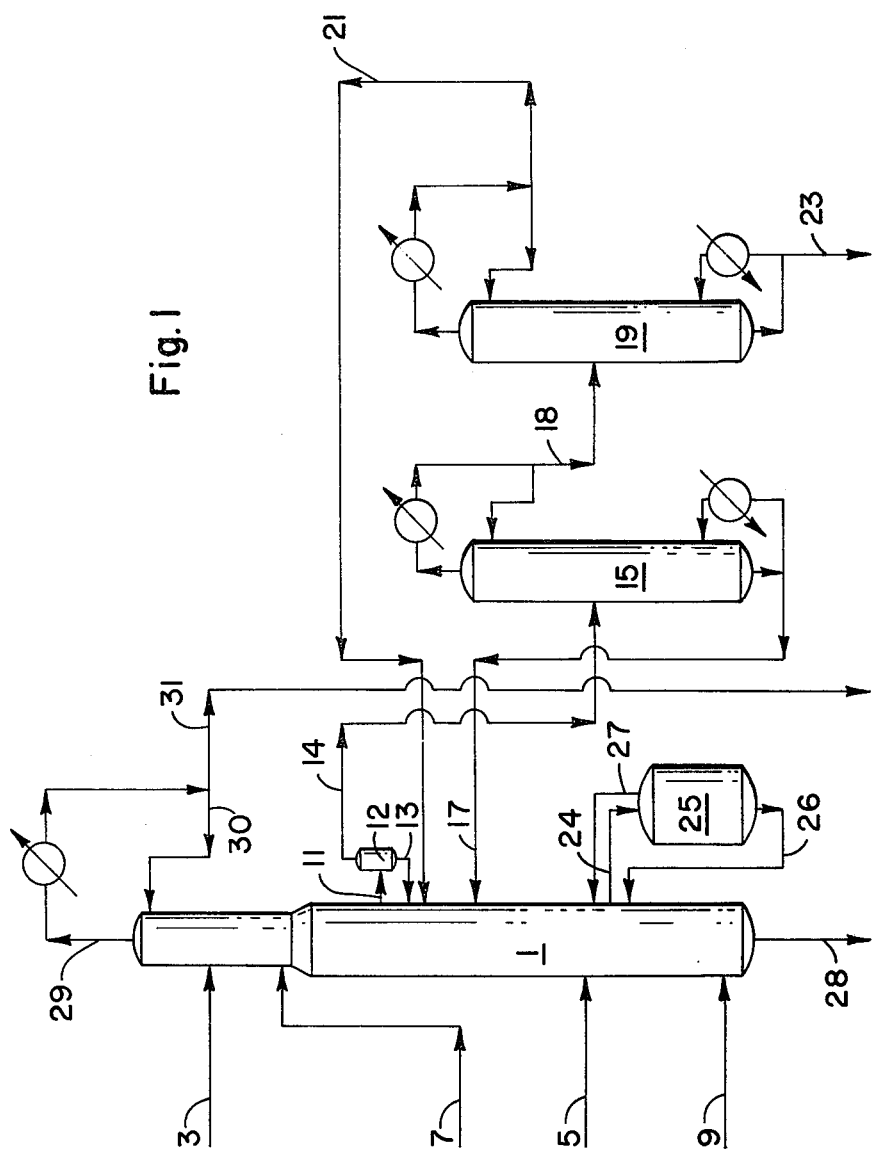
FIG. 1 is a schematic flow diagram illustrating the process of the present invention and indicating appropriate apparatus for use therein.

The present invention relates to a reactive distillation process for the production of high purity methyl acetate.

The esterification of acetic acid with methanol, in the presence of a catalyst, to produce methyl acetate and water is a well-known reaction:

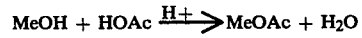

$$\text{MeOH} + \text{HOAc} \xrightarrow{\text{H}+} \text{MeOAc} + \text{H}_2\text{O}$$

In the process of the present invention, methanol (MeOH) and acetic acid (HOAc) are reacted in a single continuous reactor/distillation column combination which provides sufficient residence time to achieve high conversion of the reactants to high purity methyl acetate product. By "high reactant conversion" is meant a conversion of at least about 99%. For example, in the process of the present invention, a conversion of acetic acid of about 99.8% and a conversion of methyl alcohol of about 99.5% are achieved. The term "high purity methyl acetate" as used herein denotes a product stream containing at least about 99% methyl acetate (MeOAc). Preferably, the product stream contains at least about 99.5% MeOAc. Typically, the overhead product stream from the reactor/column contains about 99.5% methyl acetate, 0.33% H$_2$O, about 0.15% MeOH, and about 0.02% methyl propionate. Unless otherwise specified, all percentages used herein are weight percentages.

The high conversions of MeOH and HOAc to high purity methyl acetate are achieved by the counter-current flow of reactants and products. Glacial acetic acid (i.e., acetic acid containing less than about 0.5% water) is fed to the upper part of the reactor/column, and methanol is fed to the lower end of the reactor/column. The reactants flow counter-currently through the reactor/column, reacting and flashing at each stage. The removal of methyl acetate, by flashing, preferentially to the other components at each reactive distillation stage increases the extent of reaction achieved in each stage.

As methyl acetate is formed from the reactants, the formation of azeotropes also occurs. Specifically, there are formed an azeotrope of methyl acetate and water which contains about 5% water, and an azeotrope of methanol and methyl acetate which contains about 19% methanol. The extremely high product purity referred to above is achieved through the use of acetic acid as the extractive agent to break the MeOAc/H$_2$O and MeOAc/MeOH azeotropes. The removal of methanol from the methyl acetate/methanol azeotrope is also, and primarily, accomplished by reaction of the methanol with acetic acid.

The reactor/column is operated so as to provide intimate contact in the column between the acetic acid and methanol, between the acetic acid and methyl acetate/water azeotrope, and between the acetic and sulfuric acids and the methyl acetate/methanol azeotrope. By providing intimate contact between acetic acid and each of the components of the column referred to above, high conversions of reactants to product and high product purity are achieved. High purity methyl acetate is continuously removed from the top of the single reactor/column and by-product water is continuously removed from the bottom of the reactor/column.

Figure 2:
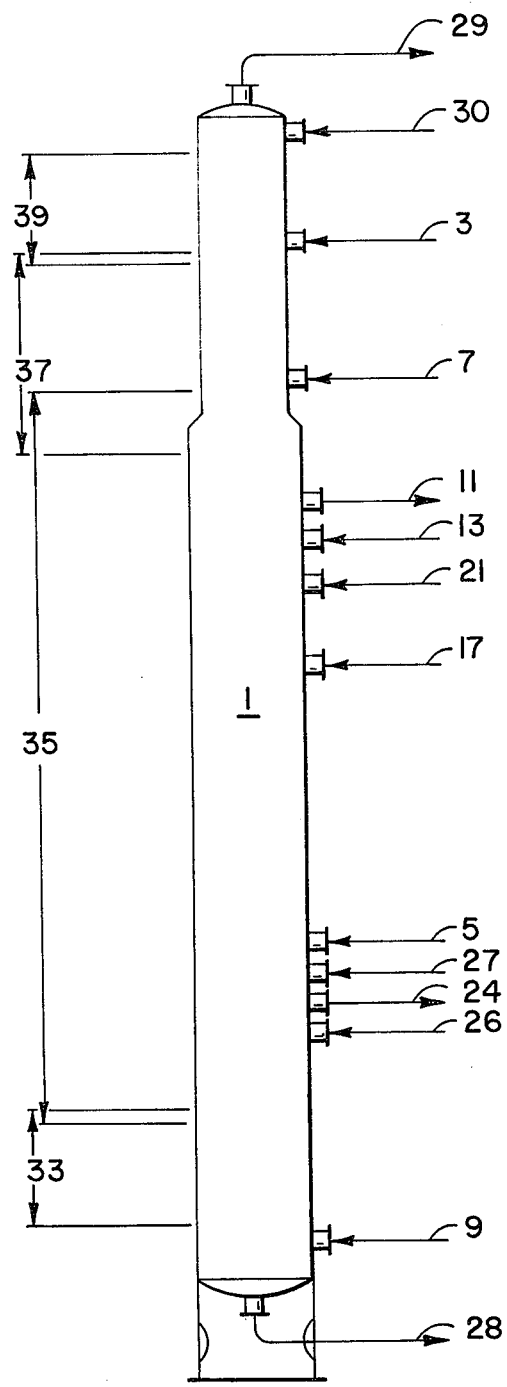
FIG. 2 is a schematic diagram of an appropriate reactive distillation column for use in the process of the present invention, indicating suitable locations of feed streams, etc.

As shown in FIG. 2 and discussed more fully hereinafter, the reactor/column consists of a methanol/water stripping section, a reactive distillation section, an extractive distillation section, and a methyl acetate/acetic acid rectification section. The presence of each of these functional sections in the reactor system and the use of acetic acid both as reactant and as extractive agent are necessary components of the process of the present invention.

The acetic acid and methanol reactants are provided to the column in approximately stoichiometric quantities. Typically, the acetic acid and methanol will be fed in a molar ratio of about 1:1. However, the term "approximately stoichiometric quantities" includes the use of an excess of methanol (e.g., a molar ratio of methanol:acetic acid in the range of about 1.1–2.0). Any excess methanol is removed from the bottom of the column with the waste water and can be recycled to the feed port following purification.

The methanol feed stream need not be pure methanol but may include water, for example, as an impurity. The introduction of a methanol/water mixture to the process of the present invention does not adversely affect the operation of the process and may substantially enhance the economics thereof, obviating the need for purification apparatus upstream.

Likewise, the glacial acetic acid which is fed to the inventive process may contain small amounts of impurities such as ethyl acetate, propionic acid, n-propyl acetate, etc.

The most effective and economical catalyst for use in the process of the present invention has been found to be sulfuric acid. Preferably, the catalyst which is employed is 95–98% sulfuric acid in aqueous solution. Other catalysts which have been used successfully include phosphoric acid and Amberlite 200 ® acidic cation exchange resin. However, when a catalyst such as phosphoric acid is used, higher catalyst concentrations and/or larger reactor sizes are required, and when a cation exchange resin requiring packed sections is utilized, complex reactor desings are involved.

The catalyst is provided to the reactor/column in a concentration sufficient to provide the desired catalytic effect. The optimal concentration of the specific catalyst system employed will become apparent to the skilled artisan. When sulfuric acid is used as the catalyst, the flow rate found to be most beneficial in the process of the present invention is about one kg of sulfuric acid per 100 kg of acetic acid feed. When higher catalyst concentrations are employed, lower hold-up times are required for a given conversion. However, higher catalyst concentrations give rise to increased corrosion rates. Conversely, lower catalyst concentrations give rise to lower corrosion rates but require longer hold-up times for a given conversion.

The catalyst (e.g., sulfuric acid) can be fed to the reactor/column together with the acetic acid feed, or it may be fed by itself at a location a few trays from the acetic acid feed plate (for example, at the lower end of the extractive distillation section). The location of the catalyst feed appears to be one factor which affects the amount of water and/or methanol present in the product. The optimal placement of the catalyst feed in the column will be apparent to one of ordinary skill in the art.

Heat can be supplied to the present process by any conventional means. Preferred methods include sparging steam into the base heater or the use of a reboiler. The use of a reboiler requires more exotic materials of construction, such as zirconium, in order to keep the corrosion rates at the base heater within a moderate range.

The highest corrosion rates are encountered in the lower half of the methanol stripping section and in the base heater. The high corrosion rates are due to the aqueous sulfuric acid present at the high temperatures that are found in the base of the column. In order to reduce the temperatures, and therefore the corrosion rates, encountered at the bottom of the reactor/column, the process can be operated by feeding an excess of MeOH to the reactor/column, as discussed above. The excess methanol can then be separated from the by-product water and catalyst in a smaller column operated at a lower pressure.

The reactor/column is commonly operated at a temperature in the reaction section of about 65 to 85° C. However, the optimal temperature for a particular process is dependent upon a number of factors, including the number of stages in the reactor/column, the desired production rate, the operating pressure, the corrosion rates which can be tolerated by the apparatus, etc. Typically, it is desirable to maintain as low a temperature as possible for a given production rate. However, for a given production rate, less catalyst is required at higher temperatures. Upon a careful consideration of all of the variables in a given process, an optimal operating temperature will become apparent to one of ordinary skill in the art.

The reactor/column is commonly operated at a pressure in the reaction section of about 100 to 200 kPa (1 to 2 atmospheres). Again, the optimal pressure is dependent upon a number of factors, but, generally speaking, operation of the process is easier and product quality is better at lower pressures.

The residence time of the reaction mixture in the column is a critical feature of the process of the present invention. The term "residence time" as used herein is defined as the clear liquid hold-up volume in the reaction trays divided by the sum of the volumetric flow rates of acetic acid and methanol. The minimum residence time which is required for high reactant conversion and high product purity depends upon the catalyst, the catalyst concentration, and the number of stages employed in a particular process. The high conversions of the reactants and the high purity of the product cannot be achieved below this minimum residence time. At a catalyst feed rate of about one kg of sulfuric acid per one hundred kg of acetic acid, the residence time for the process of the present invention is typically at least about two hours. Preferably, the residence time in the reactor is about 2.4 hours.

In a preferred embodiment, the high hold-up times required to attain the minimum residence time in the present process is achieved through the use in the reaction section of reverse flow trays having high weirs, high bubble cap risers, and large inlet and flow reversing zone sumps. A preferred design is shown in FIG. 3 and will be discussed hereinafter.

In preferred embodiments, the reflux ratio of the process of the present invention is at least about 0.75. This has been found to be the minimum reflux ratio for the inventive process below which the distillation is ineffective. As used herein, the term "reflux ratio" is defined as the ratio of the overhead reflux flow rate to the overhead product flow rate. In especially preferred embodiments, the reflux ratio is about 0.8 to 3.0 (e.g., about 1.5 to 1.7). It has been observed that conversion decreases rapidly at reflux ratios above about 2.0.

It has been observed that intermediate boiling compounds that enter the reactor/column as impurities in feeds, or that are formed as the products of reactions of impurities with reactants, accumulate in the reactor/column, particularly in the upper section of the reaction zone and throughout the extractive distillation zone. Some of these intermediate boiling compounds are methyl propionate, methyl butyrate, isopropyl acetate, etc. These compounds exhibit boiling points which are considerably higher than the boiling point of methyl acetate. However, either the compounds themselves or their water azeotropes boil at considerably lower temperatures than water. In addition, the activity coefficients in water of the compounds or their azeotropes may be quite high (e.g., as in the case of methyl propionate). Therefore, such compounds or their azeotropes tend to build up in the reactor/column. The accumulation of these intermediate boiling compounds reduces the volume in the reactor/column which is available for reaction and also reduces the extractive capability of acetic acid, thus causing lower conversions and producing a product having a higher concentration of water.

Therefore, the process of the present invention preferably further comprises removing a vapor sidedraw stream from the reactor/column, removing intermediate boiling compounds from the sidedraw stream, and returning the sidedraw stream to the column. The vapor sidedraw stream is preferably withdrawn from the middle to upper part of the reaction section of the column. Suitable apparatus is shown in FIG. 1. The vapor which is removed from the reactor/column consists mostly of methyl acetate and acetic acid but also contains intermediate boiling compounds. The vapor also contains water and methanol, which are present predominantly as azeotropes with methyl acetate. The vapor is passed through a wire mesh separator which removes any entrained sulfuric acid, which is returned to the reactor/column. The vapor is then fed to a first sidedraw column where methyl acetate and its azeotropes and the intermediate boiling compounds are taken overhead, while acetic acid and water are collected as bottoms from the column and are returned to the reactor/column. The distillate from the first column is then fed to a second column where the intermediate boiling compounds are obtained as the underflow. Methyl acetate and its azeotropes are taken as the distillate of this column and are returned to the main reactor/column.

Preferred embodiments of the process of the present invention also include the use of a hold-up tank. The reactant conversion, for a given number of trays, can be increased by feeding at least a portion of the reaction mixture from the reactor/column to a reaction tank having a large hold-up. The tank is preferably located between the reaction section and the methanol stripping section of the reactor/column. However, the location and size of the hold-up tank are not highly significant and the elimination of the hold-up tank decreases the acetic acid conversion by less than about 1%. When employed in the process of the present invention, the hold-up tank preferably provides an additional residence time of about one hour.

The methanol feed to the reactor/column can be located above, below, or at the hold-up tank. The choice of the methanol feed location depends on the water content of the methanol and on whether the methanol is fed as a liquid or vapor. The optimal point of methanol feed will be apparent to one of ordinary skill in the art.

It is difficult to achieve precise control of the reactor/column overhead and bottoms compositions simply by measuring the flow rates of the acetic acid and methanol feeds and of the distillate. These flow rates must be adjusted frequently for changes in feed and product compositions, for liquid density changes due to variations in temperature, etc. It has been found that the overhead and bottom compositions can be controlled quite easily using two temperature control loops.

The first and most important loop controls the takeoff rate (i.e., the MeOAc distillate flow rate) and typically varies it within ±5% of the target distillate flow rate. The target distillate flow rate is, of course, dependent upon the reactant flow rates. Upon determining the required reactant flow rates for the desired production level (i.e., the target distillate flow rate), the distillate flow rate is controlled so as to maintain at a preselected constant level the temperature of a point in the middle to upper part of the reaction zone. The point should be located at a position where the reaction mixture composition, particularly the water concentration, changes sharply. This control scheme assures that the reaction zone is positioned within the reaction trays (which are designed to provide high hold-up times), thus ensuring high conversion and proper extraction of $H_2O$ and MeOH. The exact temperature at which this control point is set is dictated by the concentration at which the intermediate boiling impurities are allowed to accumulate in the reactor/column. The desired temperature set point is easily determined by one skilled in the art.

A similar strategy is employed to control the MeOH feed. A second temperature feedback loop is used to vary the MeOH feed typically within about ±10% of its target rate for a given production rate during stoichiometric operation. This second control temperature is located in the lower section of the MeOH stripping section of the column, where the temperature changes rapidly with slight changes in MeOH concentration. As stated above, the methyl acetate production rate is determined by the reactant feed rates. Therefore, for a given target methyl acetate production rate, the methanol feed rate should equal the stoichiometric requirements plus the anticipated methanol loss due to the presence of methanol in the reactor/column underflow and overflow. This is what is meant by target methanol flow rate.

It is important that these flows not be varied significantly from the indicated ranges for a given production rate. The high hold-up of the reactor/column makes its responses very sluggish. Therefore, if the distillate and/or the MeOH flow rates are allowed to vary over a wider range, over-shoot and undershoot are difficult to avoid. However, when excess methanol is used, the control on the second loop can be relaxed.

The temperature controls discussed above operate to keep the reaction profile set within the reactor/column. As a result, minor amounts of water and methanol are taken overhead, and mere traces of acetic acid (typically less than 0.3%) and methanol (typically less than 0.1%) are detected in the under-flow when no excess methanol is fed to the reactor/column.

All of the remaining operating parameters can be controlled as they would be in a typical distillation column. For example, the acetic acid feed, acidic catalyst feed, and rate of flow of steam to the base of the column can be on flow control, the underflow can be on base level control, etc.

Turbine meters are recommended to measure the flows of acetic acid, methanol, and methyl acetate distillate because their accuracy allows the material balance of the process to be checked to ensure proper control of the process. Orifice meters can be used to measure the reflux flow rate, the sulfuric acid flow rate, and the steam flow to the base of the column. A back-up meter is provided in case the sulfuric acid orifice meter fails. Maintenance of steady catalyst flow has been found to be necessary for smooth operation of the process.

A continuous on-line water analyzer, calibrated for 0–10,000 ppm water in methyl acetate, can be installed on the distillate line. This instrument should have a high water concentration alarm. The information provided by such an analyzer is valuable for the smooth operation of the process and the assurance of high quality product.

It has been determined that the reactor/column should have, generally speaking, approximately 30 trays (e.g., up to about 45 trays or more) in the reaction zone. These trays are preferably of the bubble cap type. Approximately 10 trays each are required for the acetic acid rectification zone, the extractive distillation zone, and the methanol stripping zone.

The invention in its preferred embodiments will now be described with reference to the drawings. Each element is labeled consistently throughout the various drawings.

FIG. 1 depicts a flow diagram of the process of the present invention. The reactor/distillation column 1 is provided in its upper section with an inlet for glacial acetic acid which is provided to the column through feed stream 3. Methanol is fed to the lower part of the reaction section of the reactor/column through feed pipe 5. Sulfuric acid catalyst is fed through line 7 to the lower portion of the extractive distillation section of the column. Steam is applied to the base of the column through line 9.

A vapor sidedraw stream is withdrawn from the middle to upper part of the reaction section of the column through line 11. The vapor stream is passed through wire mesh separator 12, from which entrained sulfuric acid is returned to the column through line 13, and the remaining components of the vapor sidedraw stream are fed through line 14 to a first sidedraw distillation column 15. A bottoms stream comprising mostly acetic acid and water is taken from column 15 and is returned through line 17 to reactor/column 1. Methyl acetate and its azeotropes and intermediate boiling compounds are taken overhead and are fed through line 18 to a second sidedraw distillation column 19. Methyl acetate and its azeotropes are taken as the distillate from column 19 and are returned through line 21 to the reactor/column 1. The intermediate boiling compounds are obtained as the underflow from column 19 through line 23.

The reaction mixture from the lower end of the reaction section of reactor/column 1 is fed through line 24 to hold tank 25. The hold tank has a hold-up time of at least about one hour and may be used to increase the reactant conversion for a given number of trays in reactor/column 1. The reaction mixture is returned from hold tank 25 to reactor/column 1 through line 26. The hold tank product vapor is returned from hold tank 25 to reactor/column 1 through line 27.

By-product water, sulfuric acid, and excess methanol, if any, are withdrawn from the base of the column through line 28. The methyl acetate product stream is withdrawn from the top of the column through line 29. A reflux stream is returned to the column through line 30, and a product stream is taken off through line 31.

The flow diagram represented by FIG. 1 and described above is, of course, a simplified flow diagram of preferred embodiments of the process of the present invention. The apparatus utilized in the process of the present invention may additionally include vent scrubbers and other well-known apparatus.

FIG. 2 is a detail of reactor/column 1 showing the various functional sections within the column. Feedstreams for acetic acid, methanol, sulfuric acid, and steam are again represented by numerals 3, 5, 7, and 9, respectively. The vapor sidedraw stream and the corresponding return streams are indicated by numerals 11 and 13, 17, and 21, respectively. Line 24 represents a liquid sidedraw to the hold tank, and the return lines from the hold tank are indicated by lines 26 and 27. The column bottoms are removed through line 28, and the overhead is removed through line 29, with a reflux stream being returned through line 30.

The area labeled as 33 represents the approximate limits of the methanol/water stripping section of the column. In this section, methanol is stripped from the by-product water. The water is removed from the column through line 28 while the methanol ascends through the column, reacting with acetic acid as it ascends.

The region of the column designated as 35 is the reactive distillation section of the column. In this area, much of the reaction between acetic acid and methanol occurs. The methyl acetate product is flash distilled at each stage and rises through the column. During this process, methyl acetate/water and methyl acetate/methanol azeotropes are inevitably formed. These azeotropes are broken by the acetic acid which acts as an extractive agent as it descends through the column and as it reacts with the methanol.

The extractive distillation section of the column is indicated by numeral 37. In this region, which is rich in acetic acid, formation of product methyl acetate from the reactants continues to occur, and the breaking of the aforementioned azeotropes by the extractive action of the acetic acid also continues. As indicated earlier, the primary method of removal of methanol from the methyl acetate/methanol azeotrope is by the reaction of acetic acid with methanol.

The area designated as 39 is the methyl acetate/acetic acid rectification section of the column in which methyl acetate product is separated from acetic acid reactant. The acetic acid descends through the column while the methyl acetate product is taken overhead through line 29.

In one particular embodiment, for a given production rate, methanol stripping section 33 comprises 12 reverse flow-valve trays spaced 18 inches apart; reactive distillation section 35 comprises 60 reverse flow-bubble cap trays spaced 24 inches apart; extractive distillation section 37 comprises 10 crossflow-valve trays spaced 18 inches apart; and methyl acetate rectification section 39 comprises 13 crossflow-valve trays spaced 18 inches apart. Of course, such an arrangement as outlined above is not critical to the operation of the process of the present invention but is merely an example of a system which has been found by the inventors to operate efficiently.

In order to obtain the high hold-up time required by the process of the present invention, attention must be paid to the design of the trays which are employed in the reaction section of the column. A preferred design which is suitable for use in the process of the present invention is depicted in FIG. 3. The spacing 41 between vertically adjacent trays is preferably 24 inches. FIG. 3 depicts outlet weir 43 for the tray above which is preferably 5 inches in height. The outlet weir 45 for the tray shown is also preferably 5 inches in height. In order to obtain the desired flow and the maximum bubbling area, the tray includes a 15 inch high baffle 47 through the center of the tray. The tray design includes an inlet sump 48 which is preferably 10 inches deep. The flow of liquid from the inlet sump is designated by arrows 49. The liquid flows up from inlet sump 48, around baffle 44, through bubbling area 50 on one side of baffle 47, through another 10-inch sump 51 at the opposite end of the tray from inlet sump 48, passing under a 10-inch baffle 53, through bubbling area 50 on the other side of baffle 47, and over outlet weir 45, and then falls to the inlet sump of the tray below. Bubbling area 50, on both sides of baffle 47, contains a plurality of bubble caps 55. While only a few bubble caps are illustrated in FIG. 3, it is to be understood that the entire bubbling area 50 may be covered with bubble caps, the exact number and positioning of which will be apparent to one of ordinary skill in the art. In preferred embodiments, bubble caps 55 measure 4 inches in diameter and have 5-inch risers. Each tray contains on the order of 150 to 200 bubble caps.

A tray such as the one described above has been found to provide the hold-up times which are required by the process of the present invention. The high hold-up times are thus achieved through the use of reverse flow trays having high weirs, high bubble cap risers, and large inlet and flow reversing zone sumps.

The present invention provides a process for the reaction of methanol and acetic acid in a single distillation column/reactor combination. The process allows the attainment of high reactant conversions, overcomes the problems associated with azeotrope formation during the production of methyl acetate, and provides for the removal of intermediate boiling impurities. The process provides sufficient residence time to achieve high conversion of the reactants to high purity methyl acetate. The high conversion of the reactants is achieved by the countercurrent flow of reactants and products. The overhead product purity is achieved through the use of acetic acid as an extractive agent to break the methyl acetate/water azeotrope and as reactant and extractive agent to break the methyl acetate/methanol azeotrope. The removal of methanol from the azeotrope is primarily accomplished by reaction of methanol with acetic acid.

The invention has been described in detail with particular reference to preferred embodiments thereof, but it will be understood that variations and modifications can be effected within the spirit and scope of the invention.

We claim:
1. A process for the production of high purity methyl acetate from methanol and glacial acetic acid wherein said acetic acid functions both as reactant and as extractive agent, said process comprising the steps of
   (a) selecting a design for a single reactive distillation column and a residence time thereof to provide intimate contact sufficient to enable said acetic acid to be used both as a reactant and as an extractive agent within said column,
   (b) countercurrently flowing approximately stoichiometric quantities of acetic acid and methanol through said single reactive distillation column in the presence of a catalytic amount of an acidic catalyst so as to provide intimate contact in said column between said acetic acid and methanol, between said acetic acid and methyl acetate/water azeotrope, and between said acetic acid and methyl acetate/methanol azeotrope, the residence time in said column being sufficient to accomplish high reactant conversion and to obtain high purity methyl acetate, and
   (b) continuously removing high purity methyl acetate from the top of said single column and continuously removing water from the bottom of said column.
2. The process of claim 1 wherein said acidic catalyst is selected from sulfuric acid, phosphoric acid, acidic cation exchange resin, and mixtures thereof.
3. The process of claim 1 wherein said acidic catalyst comprises sulfuric acid.
4. The process of claim 1 wherein the reflux ratio is about 0.8 to 2.0.
5. The process of claim 1 wherein the reflux ratio is about 1.5 to 1.7.
6. The process of claim 1 wherein the methyl acetate product is at least about 99% pure.
7. The process of claim 1 wherein the methyl acetate product is at least about 99.5% pure.
8. The process of claim 1 which further comprises removing a vapor sidedraw stream from said column, removing intermediate boiling compounds from said sidedraw stream, and returning said sidedraw stream to said column.
9. The process of claim 8 wherein said vapor sidedraw stream is withdrawn from the middle to upper part of the reaction section of said column.
10. The process of claim 8 wherein said intermediate boiling compounds comprise methyl propionate, methyl butyrate, isopropyl acetate, and mixtures thereof.
11. The process of claim 1 which further comprises feeding at least a portion of the reaction mixture from said column to a hold-up tank having a residence time of at least about one hour and returning the reaction mixture to said column.

12. The process of claim 1 which further comprises controlling the methanol feed rate so as to maintain at a preselected constant level the temperature of a point located in the column below the methanol feed and controlling the distillate flow rate so as to maintain at a preselected constant level the temperature of a point located in the middle to upper part of the reaction section of the column.

13. The process of claim 12 wherein the methanol feed rate is controlled within about ±10% of the target methanol flow rate.

14. The process of claim 12 wherein the distillate flow rate is controlled within about ±5% of the target distillate flow rate.

15. A process for the production from methanol and glacial acetic acid of methyl acetate which is at least about 99% pure, wherein said acetic acid functions both as reactant and as extractive agent, said process comprising the steps of
   (a) selecting a design for a single reactive distillation column and a residence time thereof to provide intimate contact sufficient to enable said acetic acid to be used both as a reactant and as an extractive agent within said column,
   (b) countercurrently flowing approximately stoichiometric quantities of glacial acetic acid and methanol through said single reactive distillation column in the presence of a catalytic amount of sulfuric acid so as to provide intimate contact in said column between said acetic acid and methanol, between said acetic acid and methyl acetate/water azeotrope, and between said acetic acid and methyl acetate/methanol azeotrope, the residence time in said column being sufficient to accomplish high reactant conversion and to obtain high purity methyl acetate, and the reflux ratio being about 0.8 to 2.0;
   (c) removing intermediate boiling compounds from a vapor sidedraw stream which is continuously removed from and returned to said column; and
   (d) continuously removing said high purity methyl acetate from the top of said column and continuously removing water from the bottom of said column.

16. The process of claim 15 wherein said reflux ratio is about 1.5 to 1.7.

17. The process of claim 15 wherein said methyl acetate product is at least about 99.5% pure.

18. The process of claim 15 wherein said intermediate boiling compounds comprise methyl propionate, methyl butyrate, isopropyl acetate, and mixtures thereof.

19. The process of claim 15 which further comprises feeding at least a portion of the reaction mixture from said column to a hold-up tank having a residence time of at least about one hour and returning the reaction mixture to said column.

20. The process of claim 15 wherein said vapor sidedraw stream is withdrawn from and returned to the middle to upper part of the reaction section of said column.

21. The process of claim 15 wherein said sulfuric acid is fed to the column at a rate of about 1 kg of sulfuric acid per 100 kg of acetic acid.

22. The process of claim 21 wherein the residence time is at least about 2 hours.

23. The process of claim 21 wherein the residence time is at least about 2.4 hours.

24. The process of claim 15 which further comprises controlling the methanol feed rate so as to maintain at a preselected constant level the temperature of a point located in the column below the methanol feed and controlling the distillate flow rate so as to maintain at a preselected constant level the temperature of a point located in the middle to upper part of the reaction section of the column.

25. The process of claim 24 wherein the methanol feed rate is controlled within about ±10% of the target methanol flow rate.

26. The process of claim 24 wherein the distillate flow rate is controlled within about ±5% of the target distillate flow rate.

27. A process for the production from methanol and glacial acetic acid of methyl acetate which is at least about 99.5% pure, wherein said acetic acid functions both as reactant and as extractive agent, said process comprising the steps of
   (a) selecting a design for a single reactive distillation column and a residence time thereof to provide intimate contact sufficient to enable said acetic acid to be used both as a reactant and as an extractive agent within said column,
   (b) countercurrently flowing approximately stoichiometric quantities of glacial acetic acid and methanol through said single reactive distillation column in the presence of sulfuric acid, which is fed to the column at a rate of about 1 kg of sulfuric acid per 100 kg of acetic acid, so as to provide intimate contact in said column between said acetic acid and methanol, between said acetic acid and methyl acetate/water azeotrope, and between said acetic acid and methyl acetate/methanol azeotrope, the residence time in said column being at least about 2.4 hours and the reflux ratio being about 1.5 to 1.7;
   (c) removing intermediate boiling compounds comprising methyl propionate, methyl butyrate, isopropyl acetate, and mixtures thereof from a vapor sidedraw stream which is continuously removed from and returned to the middle to upper part of the reaction section of said column;
   (d) controlling the methanol feed rate within about ±10% of the target flow rate so as to maintain at a preselected constant level the temperature of a point located in the column below the methanol feed and controlling the methyl acetate distillate flow rate within about ±5% of the target flow rate so as to maintain at a preselected constant level the temperature of a point located in the middle to upper part of the reaction section of said column; and
   (e) continuously removing said high purity methyl acetate from the top of said column and continuously removing water from the bottom of said column.

28. The process of claim 27 which further comprises feeding at least a portion of the reaction mixture from said column to a hold-up tank having a residence time of at least about one hour and returning the reaction mixture to said column.

* * * * *